United States Patent
Zarli et al.

(10) Patent No.: US 11,535,581 B2
(45) Date of Patent: Dec. 27, 2022

(54) METHOD AND APPARATUS TO PRODUCE FATTY ACIDS FROM METHYL ESTERS THROUGHOUT NON-CATALYTIC PROCESS

(71) Applicant: NEXTCHEM S.P.A., Rome (IT)

(72) Inventors: Antonio Zarli, Rome (IT); Paolo De Filippis, Rome (IT); Marco Scarsella, Rome (IT)

(73) Assignee: NEXTCHEM S.P.A., Rome (IT)

( * ) Notice: Subject to any disclaimer, the term of this patent is extended or adjusted under 35 U.S.C. 154(b) by 2 days.

(21) Appl. No.: 17/272,193

(22) PCT Filed: Aug. 30, 2018

(86) PCT No.: PCT/IT2018/000111
§ 371 (c)(1),
(2) Date: Feb. 26, 2021

(87) PCT Pub. No.: WO2020/044380
PCT Pub. Date: Mar. 5, 2020

(65) Prior Publication Data
US 2021/0363090 A1    Nov. 25, 2021

(51) Int. Cl.
*C07C 51/09* (2006.01)
*C11C 1/04* (2006.01)

(52) U.S. Cl.
CPC .............. *C07C 51/09* (2013.01); *C11C 1/04* (2013.01)

(58) Field of Classification Search
CPC ......... C07C 51/09; C07C 53/126; C11C 1/04; C11C 1/08
See application file for complete search history.

(56) References Cited

U.S. PATENT DOCUMENTS

| | | | |
|---|---|---|---|
| 4,262,140 A | * | 4/1981 | Bott .................. C07C 51/44 203/28 |
| 4,302,595 A | * | 11/1981 | Schoengen ............ C07C 51/09 562/483 |
| 5,440,061 A | | 8/1995 | Gibson |
| 5,508,455 A | | 4/1996 | Gibson |
| 6,646,146 B1 | | 11/2003 | Sinnema et al. |

(Continued)

FOREIGN PATENT DOCUMENTS

| | | | | |
|---|---|---|---|---|
| GB | 594141 A | * | 4/1947 | ............ C11C 1/04 |
| WO | 94/14743 | | 7/1994 | |
| WO | 2015/038885 | | 3/2015 | |

(Continued)

OTHER PUBLICATIONS

International Search Report for PCT/IT2018/000111 dated May 10, 2019, 3 pages.

(Continued)

*Primary Examiner* — Yate' K Cutliff
(74) *Attorney, Agent, or Firm* — Nixon & Vanderhye

(57) ABSTRACT

An autocatalytic process for producing fatty acids from fatty acids methyl esters with an overall conversion higher than 90% which includes multiple hydrolysis reactions in series, in purely thermal conditions, with intermediate separation of phases after each hydrolysis reaction and before the subsequent, operating in excess of water, in order to separate the methanol/water phases from the equilibrium phase and favor the formation of fatty acids product.

26 Claims, 2 Drawing Sheets

(56) References Cited

U.S. PATENT DOCUMENTS

2019/0211282 A1* 7/2019 Bauer .................... C11C 3/003

FOREIGN PATENT DOCUMENTS

| WO | 2018/007022 | | 1/2018 | | |
|---|---|---|---|---|---|
| WO | WO2018/007022 | * | 1/2018 | ............... | C11C 1/04 |

OTHER PUBLICATIONS

Written Opinion of the ISA for PCT/IT2018/000111 dated May 10, 2019, 5 pages.
Written Opinion of the IPEA for PCT/IT2018/000111 dated Dec. 13, 2019, 5 pages.
International Preliminary Report on Patentability for PCT/IT2018/000111 dated Jun. 30, 2020, 13 pages.

\* cited by examiner

METHOD AND APPARATUS TO PRODUCE FATTY ACIDS FROM METHYL ESTERS THROUGHOUT NON-CATALYTIC PROCESS

This application is the U.S. national phase of International Application No. PCT/IT2018/000111 filed Aug. 30, 2018 which designated the U.S., the entire contents of which are hereby incorporated by reference.

BACKGROUND OF THE INVENTION

Field of the Invention

The present invention relates to a process and apparatus for producing, in a simple and economic way, fatty acids from fatty acids methyl esters, with an overall conversion higher than 90%, wherein an hydrolysis reaction of methyl esters, in purely thermal condition, without catalyst, is carried out in steps in order to overcome the equilibrium reaction limits due to the solubility of produced methanol in both liquid phases, i.e. methyl esters and water phases, using a set of a number of reactors in series, with each step immediately followed by a liquid/vapor phase separator.

According to the invention the fatty acid methyl esters are preferably a mixture of C6-C18 methyl esters.

The multi-reaction unit works with the concept to have integrated with the reaction process unit a methanol rectification column to produce pure methanol and recover the excess of water to be recirculated back to the reaction unit.

A distillation column(s) system is also integrated in the overall production process to separate fatty acids at required purity over 99% by weight and to recover and recycle the unreacted methyl esters back to the hydrolysis reaction unit.

DESCRIPTION OF THE RELATED ART

Methods of Production of Fatty Acids Starting from Methyl Esters

Literature is reporting several methods and processes for the production of fatty acids from methyl esters. Today none of them is still established as an industrial practice. Below are some known processes briefly presented and discussed.

Saponification/Acidification

The starting methyl ester can be subjected to saponification with a base (i.e. NaOH) and afterwards, the resulting salt can undergo acidification with an acid (i.e. H2SO4) to obtain the fatty acid, as seen in reactions 1.1 and 1.2.

The final product is obtained after washing, drying and distillation of the raw reaction mixture.

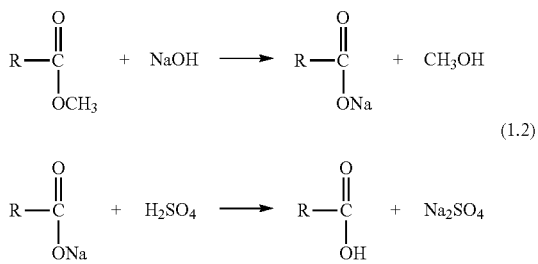

The disadvantages of this process include high production process cost and the presence of reaction intermediates such as soaps that must be removed from the main process stream.

Alkaline Hydrolysis

In this process the methyl esters are broken down into fatty acids and methanol at high temperatures and pressures using a basic catalyst. In the reaction is the formation of soap that acts as an emulsifier to promote contact between phases.

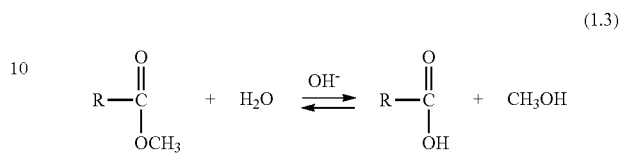

The disadvantages of this process are due to the formation of foams and to the need to separate and purify the final product from the catalyst.

Enzymatic Hydrolysis

The hydrolysis of esters can be promoted by enzymes. These act like catalysts bringing in emulsion and hydrolyzing the reagents. The advantage of this process is that it works at low temperatures and produces light-colored fatty acids, the disadvantage however is given by the fact that the hydrolysis remains incomplete, require long reaction times and the choice of the enzymes to be used is a critical step in the development of this type of process.

Non-Catalytic Hydrolysis

Conceptually, esters can be hydrolyzed without catalysts at high pressure and high temperatures (e.g. 700 psig and 250° C.). This process has the essential advantage to obtain products not contaminated with soaps, or acidic substances or other catalytic components.

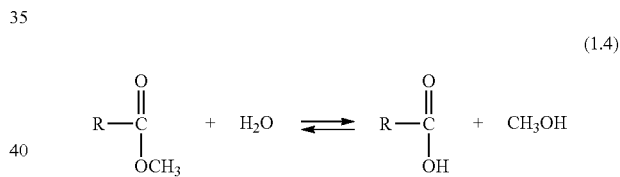

The disadvantage is the requirement to use equipment that need to be designed to withstand to the operating conditions, furthermore there is the need to remove the methanol from the reaction phase to obtain conversions suitable for industrial processes.

STATE OF PRIOR ART

In the P & G patent U.S. Pat. No. 5,508,455 A released in 1996 a method is presented as production of fatty acids through the hydrolysis of methyl esters catalyzed by acids.

The patent in question is a modification of the U.S. Pat. No. 5,440,061 A of 1995 in which, in addition to the acid catalyst, DMSO (dimethyl sulfoxide) was used as a solvent.

In the U.S. Pat. No. 6,646,146 B1 of Haltermann Ascot GmbH [38], now part of the Dow group, it is disclosed a liquid phase process for the direct hydrolysis of a fatty acid ester to the corresponding fatty acid and alcohol in the presence of a catalyst, wherein the fatty acid in the liquid phase is contacted with steam in the presence of a compound of a metal that is capable of forming a soap with a large hydration shell as a catalyst.

In the EP Patent 0 675 867 B1 of The Procter & Gamble Company, it is disclosed a process of preparing fatty acids from preferably methyl esters via acid-catalyzed hydrolysis by using specific ratios of water/-ester/acid catalyst (surface active) to form a single phase reaction mixture wherein the initial stoichiometric ratio of water to ester is at least 1:1, and wherein the initial molar ratio of any residual amount of carboxylic acid to ester is less than 1:1, preferably less than 0.5:1 especially when said carboxylic acid contains less than 6 carbon atoms.

In view of the above, it is evident the need for a method and a process to produce fatty acids from methyl esters, in a simple and economic way, in autocatalytic conditions, without the addition of catalyst.

SUMMARY OF THE INVENTION

As previously stated, the hydrolysis reaction is an equilibrium reaction, therefore in order to shift the conversion in favor of the products it is necessary to work in excess of a reagent and/or remove at the same time one of the products.

In the industrial non-catalytic continuous process of fat hydrolysis, the removal of reaction products takes place continuously being the glycerol highly soluble in the excess water.

The present invention relates to an autocatalytic hydrolysis reaction where to overcome the limits given by the reaching of the equilibrium conditions wherein the produced methanol is soluble in both liquid phases, the reaction is carried out in steps.

According to the present invention, being the methanol produced soluble in methyl esters and water phases, in order to separate the methanol/water phase from the organic phase and favor the formation of Fatty Acids product with an advantageous overall yield, a set of a number of reactors in series, with each step immediately followed by a liquid/vapor phase separator is used.

In the present invention temperature, pressure and ratio of reactants, methyl esters and water, have been selected to better improve the hydrolysis reaction yield.

Furthermore the multi-reaction unit works with the concept to have integrated with each hydrolysis reaction process unit a methanol rectification column to produce pure methanol and recover the excess of water to be recirculated back to the reaction unit.

Furthermore a distillation column(s) system to purify the obtained fatty acids to the required commercial specification is also integrated in the overall production process to separate fatty acids at required purity and to recover and recycle the unreacted methyl esters back to the reaction unit.

The fatty acids methyl ester can be selected from any of a variety of fatty acids methyl ester.

It is preferable, however, if the fatty acid portion of the fatty acids methyl esters are medium chain fatty acids as C6-C18, particularly C8-C10.

Advantage of the Invention

The present invention is advantageous as an environmentally friendly not using any catalyst and not producing any liquid or solid stream to be treated. Furthermore could increase the production of the market highly requested short chain fatty acids using the less favorably marketable related fatty acids methyl ester.

Furthermore, the possibility of converting, at low cost, fatty acids methyl esters in fatty acids would allow to exploit the production surpluses of methyl ester cuts C6-C18, in particular C8-C10, to convert them into the relative fatty acids, most requested by the market as intermediates.

The large increase in production of C12-C14 fatty alcohols, products for hydrogenation of the C12-C14 methyl esters, observed over the last 10 years, has generated higher quantities of by-product, which are not aligned with market demand.

DETAILED DESCRIPTION OF THE INVENTION

Figure 1:
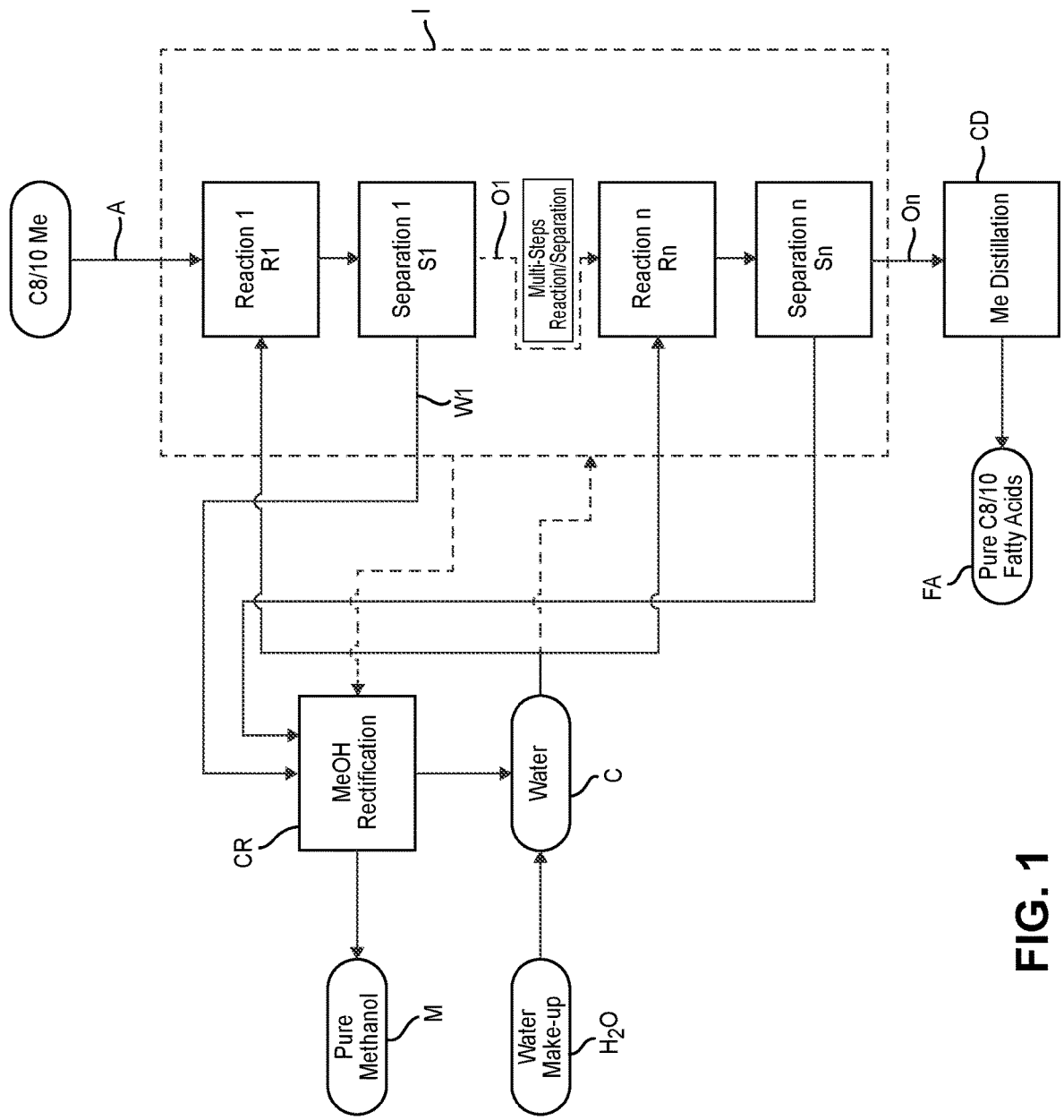
FIG. 1 is a block diagram of the multistep non-catalytic hydrolysis process of fatty acids methyl esters with intermediate phase separation process and a final distillation step to obtain a commercial quality with purities of the C8-C10 fatty acids above 99% by weight.

The present invention relates to a method and an apparatus based on multiple reactions in series with intermediate separation of phases after each reaction and before the subsequent one.

This method has shown the potentiality to obtain the highest reaction conversion yield achievable.

The present invention will allow developing a proper process for making fatty acids from fatty acid methyl esters; experimental tests have been conducted in order to define the optimal operating conditions.

The most favorable ratio and the most appropriate reaction operating condition as per pressure and temperature have been determined by a detailed study of the reaction kinetic.

Experimental Tests

To calculate the maximum conversion obtainable from the methyl ester C8-10, three consecutive tests on the same charge were conducted.

After each reaction, the phases are separated after a sufficient time and consecutively only the organic phase was taken (containing mainly methyl esters, fatty acids and a part of methanol).

A quantity of water has been added to the sample to keep the ratio by weight water/methyl ester C8-10 equal to 0, 9.

These operations allow you to push the reaction towards higher conversions, since the amount of methanol present is lower than that of equilibrium.

Test 1

Hydrolysis reaction of a mixture of C8-C10 methyl esters were conducted, under stirring conditions, in a sealed high pressure stainless steel reactor at temperatures ranging from 180 and 250° C. The reactions were conducted in autocatalytic conditions without the addition of catalysts. In all the tests a water/C8-C10 methyl esters ratio equal to 0.1 on weight basis was adopted. Each test was repeated for increasing time until the equilibrium value was reached.

The experimentation showed that the equilibrium was reached for time ranging from 1000 and 150 minutes being the shorter time at the temperature of 250° C. in table 1 the results of the experimentation.

TABLE 1

| Temperature (° C.) | Time necessary to equilibrium conditions (min) | Total percentage of fatty acids % wt at equilibrium conditions |
|---|---|---|
| 180 | 950 | 27.6 |
| 200 | 600 | 28.3 |
| 220 | 250 | 30.5 |
| 250 | 150 | 34.9 |

Test 2

Hydrolysis reactions of a mixture of C8-C10 methyl esters were conducted autocatalytically, under stirring conditions, in a sealed high pressure stainless steel reactor at fixed temperature of 250° C. using different water/C8-C10 methyl esters weight ratios until reaching the equilibrium conditions. In all the test the reaction time was maintained constant and equal to 180 minutes. The results are reported in table 2.

TABLE 2

| H2O/Me weight | C8 Methyl Ester % Weight | C10 Methyl Ester % Weight | C8 Fatty Acids % Weight | C10 Fatty Acids % Weight | Total Fatty Acids % Weight |
|---|---|---|---|---|---|
| 0.1 | 39.3 | 26.4 | 22.3 | 12.0 | 34.9 |
| 0.3 | 30.4 | 19.8 | 31.2 | 18.6 | 49.3 |
| 0.6 | 23.7 | 15.4 | 37.9 | 23.0 | 61.6 |
| 0.9 | 19.1 | 12.2 | 42.6 | 29.1 | 72.0 |

As evident from the table, in batch reactor, even using large water excess, it is not possible to reach the complete hydrolysis of the methyl esters.

Test 3

In order to increase the hydrolysis of C8-C10 methyl esters, three consecutive batch on the same charge were conducted. The reactions were carried out auto-catalytically at a temperature of 250° C. for 180 min. The water/C8-C10 methyl esters ratio was maintained constant and equal to 0.9 by weight. After each reaction step, aqueous and organic phase were let to separate. The aqueous phase was discharged while the organic phase, containing mainly methyl esters, fatty acids and a part of methanol, was retained and used as charge for a subsequent hydrolysis step. Before starting the new reaction step, a quantity of water has been added to the sample to keep the ratio by weight water/methyl ester C8-10 equal to 0.9.

These operations allow to shift the reaction towards higher conversions, since the amount of methanol present is lower than that of equilibrium.

The results after each step are reported in table 3

TABLE 3

| Step percentage | Total fatty acids % wt |
|---|---|
| 1 | 72.0 |
| 2 | 84.8 |
| 3 | 92.2 |

The use of a multi-step reaction allow to increase the amount of C8-C10 acid in the solution, but even in this case it is not possible to obtain a complete hydrolysis for C8-C10 methyl esters.

In view of the results obtained, it is an object of the present invention a method for producing fatty acids from fatty acids methyl esters with an overall conversion higher than 90% by weight, comprising multiple hydrolysis reactions in series with intermediate separation of phases after each hydrolysis reaction and before the subsequent, operating in excess of water, in order to separate the methanol/water phases from the equilibrium phase and favor the formation of Fatty acids product.

This method to operate in excess of water allows the reaction to reach higher conversion rates than that of equilibrium diluting the amount of methanol present to be lower.

Preferably the quantity of water to be add (that must been added) in each hydrolysis reaction step must be such as to keep the ratio water/methyl esters by weight equal to 0.9.

Downstream of every reaction the phases are separated and consecutively only the organic phase containing mainly methyl esters, fatty acids and a part of methanol was withdrawn and analyzed before to be fed as reactant in the subsequent reaction step.

The results obtained at the end of the experimental test campaign are showing that in less than 3 hours, working in the temperature range 200-250 C the maximum conversion is achieved. The equilibrium constant varies little with temperature, showing that the reaction is weakly endothermic.

The temperature increases from 180 to 250 C does not involve large variations in terms of feed conversion, but has an important role in reaction kinetics.

Using reagents in stoichiometric ratio, conversions are achieved in the order of 30%.

The use of ratio water/Methyl esters by weight equal to 0.9 allows achieving, in the first reaction step, a conversion of more than 70%, highlighting a considerable increase. Through the use of reactors in series with a liquid-liquid separation between one stage and the subsequent one the method is able to achieve a 90-92% conversion confirmed by the double comparison between titration and gas chromatograph.

As highlighted here above, the critical step of the reaction consists of inter-stage separation. More methanol is separated higher conversion is reachable.

In the preferred embodiment of the invention, the methanol separation is provided after each hydrolysis reactor throughout a Vapor-Liquid-Liquid separation. The terms "comprises/comprising" where used in this specification is taken to specify the presence or addition of one or more other features, integers, steps, components or group thereof.

It was underlined that the results of the experimental test campaign does not permit to obtain a hydrolysis for C8-C10 methyl esters over the 92% of purity for C8-C10 ester.

To verify the possibility to obtain a commercial quality with purities of the C8-10 Fatty Acids above 99% by weight, distillation test have been carried out in a lab scale distillation column.

Distillation

The distillation was conducted under vacuum at a total pressure of 0.02 bar. In this conditions the methyl esters are removed when reaching a head temperature of 109° C. This light cut being a mixture of unreacted C8-10 Methyl Ester can be recycled to the reaction step to maximize the overall process yield. The distillation of C8 and C10 acids ended when the head temperature reach the 128° C. In this conditions the purities achieved after the test were above 99.5% as C8-10 Fatty Acids.

Consequently, according to a feature of the present invention, it is provided to operate the distillation of the organic phase containing C8-C10 fatty acids out coming from the last separator.

In view of that, according to a further feature of the invention, in order to reach C8-C10 fatty acids at a purity above 99% by weight, it is provided to operate the distillation of the organic phase containing C8-C10 fatty acids out coming from the last separator. The distillation is carried out by a distillation column under vacuum, the pressure and temperature being selected to better improve the hydrolysis yield, as disclosed further on.

Furthermore the multi-reaction unit works with the concept to have integrated with each hydrolysis reaction process unit a methanol rectification column to produce pure methanol and recover the excess of water to be recirculated back to each reaction unit.

Use of Shorter Fatty Acids to Hydrolyze Longer Fatty Acid Methyl Esters

Esters hydrolysis is strongly dependent from the length of the organic acid. As general rule the increase of the carbon atoms in the organic chain decreases the water ester compatibility and consequently increase the difficulties to obtain a complete hydrolysis of the ester. In particular for the C8-C10 mixture it was observed that also starting from a equimolecular ester mixture, at the end of each hydrolysis step the amount of unconverted C10 is always 2 to 5 point % higher than the amount of C8 ester. It was also observed that the hydrolysis of a C8-C10 fatty acid methyl esters mixture containing low percentages of C10 esters, produces as expected a decrease in the amount of C10 esters, but surprisingly an almost equal amount of C8 ester appear. This clearly indicates that a transesterification happens together with the hydrolysis.

This aspect could be of big importance in complex mixtures of medium and long fatty acid methyl esters, where it is possible to take advantage from this effect due to the redistribution of methyl esters toward the shorter fatty acids, increasing the hydrolysis of the longer ones. As an example, can be considered the hydrolysis of mixtures of C8-C12. With an hydrolysis process, even multi-steps, at the end small amount of C12 esters are presents. Furthermore, the amounts of C12 not hydrolyzed at the end of the process can't be separated by distillation due to the overlap of the distillation temperature with the C10 acid, preventing the production of high purity acids mixture.

In this case the described effect can be crucial for hydrolyzing the C12 ester and obtain a high purity acid mixture. At the scope it is possible to separate all the light esters by distillation, then submit the residual fraction to a new hydrolysis step and re-distillate the light ester.

With reference to the drawings, according to the preferred embodiment of the invention, the block diagram described in FIG. 1 comprises at least two or more consecutive step, wherein the product of an autocatalytic hydrolysis reaction R1 to Rn is sent to a corresponding liquid/vapor phase separators S1 to Sn.

In a possible procedure for carrying out the process of this invention, an amount of a fatty acid ester A preferably C8/10 Methyl ester, is supplied to a reactor R1. After the first hydrolysis reaction step 1, aqueous W1 and organic phase O1 where let to separate, using the organic phase O1 as charge for the subsequent hydrolysis reactor R2 while the aqueous phase W1 is directed to a methanol rectification column CR to produce pure methanol M and recover in a tank C the excess of water to be recirculated back to each reaction unit R2 in order to keep the ratio by weight water/methyl ester C8-10 in a range of 0.4-1.5, preferably 0.7-1.2, more preferably equal to 0.9.

From the bottom of the last separator Sn, the organic phase On containing a mixture of unreacted C8-10 Methyl Ester is directed to a distillation column CD to separate fatty acids at required purity over 99% by weight. The distillation is conducted under vacuum at a total pressure in the range of 0-0.5 bar.

Figure 2:
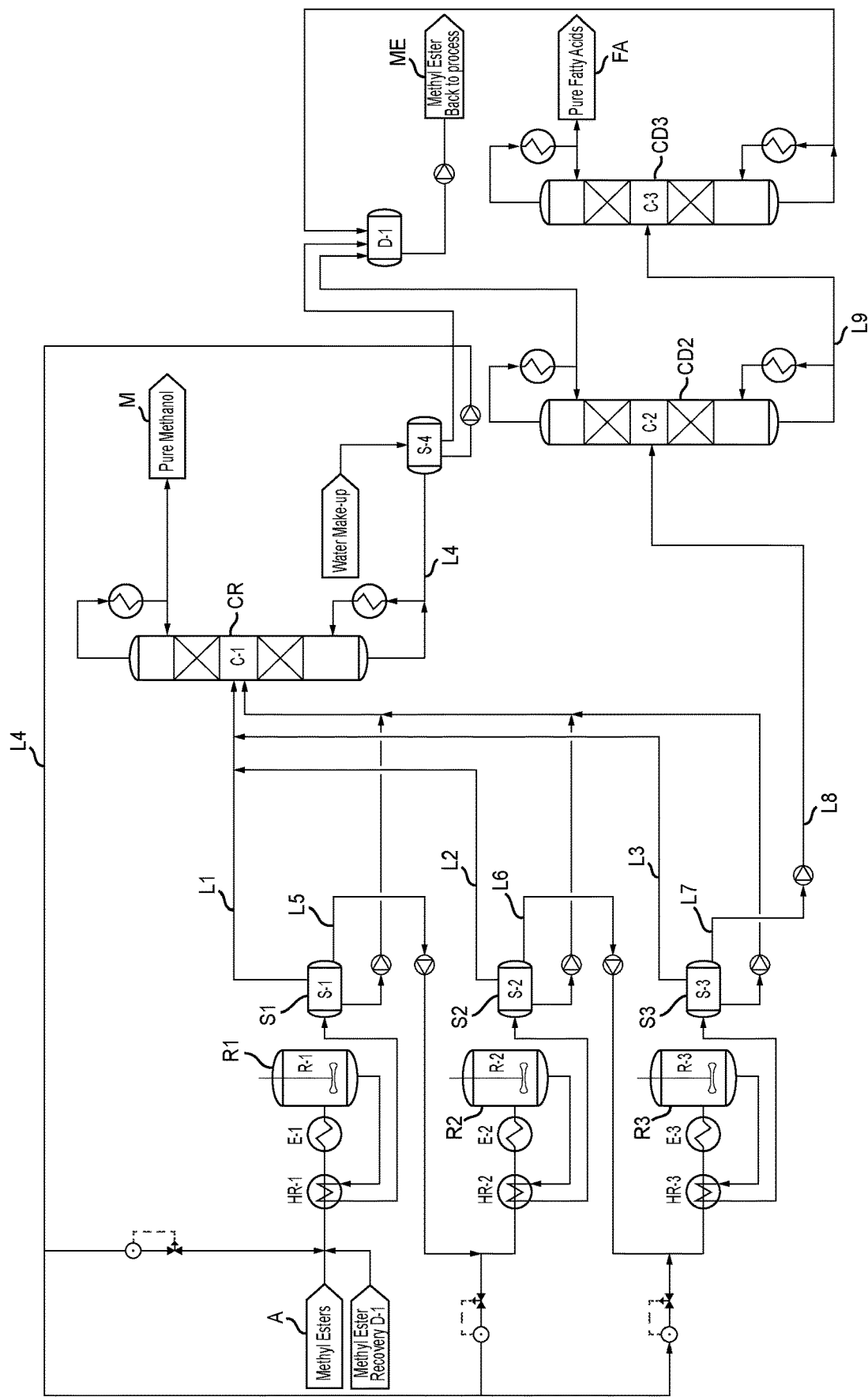
FIG. 2 shows an apparatus according to a preferred embodiment of the invention with three electrolysis reactors, three liquid/vapor phase separators, a methane/water distillation column to produce pure methanol, and two distillation columns in series to separate fatty acids at required purity

A specific embodiment of the invention is described in FIG. 2, however this invention may be designed in many different forms and should not constructed as limited to the embodiment set for herein.

Rather, this embodiment is provided so that the disclosure will be trough and complete and will full convey the scope of the invention to those skilled in the art.

The apparatus showed in FIG. 2 comprises three hydrolysis reactor R1,R2,R3, in series, wherein each reactor is immediately followed by a liquid/vapor phase separator S1,S2,S3. The methyl ester stream coming into each reactor 1.2 and 3 is heated by a corresponding Heater E1, E2 and E3. A methanol/water distillation column CR receives the stream L1,L2,L3 out coming from the single separator S1,S2 and S3 to produce pure methanol M and recover the excess of water L4 to be recirculated back to the reaction units.

From separators S1 and S2 the organic phase containing mainly methyl esters, fatty acids and a part of methanol are fed as reactant in the subsequent reactors R2 and R3, lines L5,L6 while the stream coming out from the last separator S3 fed two methyl ester distillation columns CD2,CD3 in series through lines L8,L9, obtaining pure fatty acids FA and methyl ester ME to back to process.

Heat recovery Exchangers HR-1, HR2 and HR3 are provided upstream the Heaters E1,E2 and E3.

The above-described exemplary embodiments are given only for the purpose of illustration and those skilled in the art will appreciate that the conceptions and specific embodiments disclosed in the foregoing description may be readily utilized as a basis for modifying or designing other embodiments for carrying out the same purpose of the present disclosure. Accordingly, those skilled in the art will also appreciate that the scope of the present disclosure is not limited by the exemplary embodiments.

The invention claimed is:

1. An autocatalytic process for producing fatty acids from fatty acids methyl esters in a number of reactor units and a number of Vapor/Liquid/Liquid separators, wherein the process has an overall conversion higher than 90%, the process comprising:
   multiple hydrolysis reactions in series, in purely thermal conditions;
   intermediate separation of phases after each hydrolysis reaction and before the subsequent, operating in excess of water;
   formation of fatty acids product with achievement of an equilibrium phase; and
   separation of the methanol/water phases from the equilibrium phase in order to favor the formation of fatty acids product,
wherein a ratio by weight water/methyl ester in each hydrolysis reaction is keeping in the range of 0.4-1.5 and wherein the number of reactors and the number of Vapor/Liquid/Liquid separators are at least three.

2. The autocatalytic process according to claim 1 wherein the ratio by weight water/methyl ester in each hydrolysis reaction is equal to 0.9.

3. The autocatalytic process for producing fatty acids from fatty acids methyl esters with an overall conversion higher than 90% according to claim 1, further comprising integrating with the hydrolysis reaction process a methanol rectification step to produce pure methanol and recover the excess of water to be recirculated back to the reaction unit.

4. The autocatalytic process for producing fatty acids from fatty acids methyl esters with an overall conversion higher than 90% according to claim 1, further comprising operating a distillation of an organic phase containing C8-C10 fatty acids out coming from a last separator.

5. The autocatalytic process for producing fatty acids from fatty acids methyl esters with an overall conversion higher than 90% according to claim 1, further comprising:
   a) carrying out a hydrolysis reaction of a mixture of C8-C10 methyl esters, under stirring conditions, in a sealed high pressure stainless steel reactor (R1) at a temperatures ranging from 100 and 350° C., maintaining constant in the range of 0.4-1.5 by weight a C8-C10 methyl esters/water ratio;
   separating aqueous and organic phase, containing mainly methyl esters, fatty acids and a part of methanol, through a first Vapor/Liquid/Liquid separator (S1);
   b) using the organic phase of a) as charge for a second hydrolysis step, in a consecutive hydrolyzing reactor (R2), adding a quantity of water to the sample to keep the ratio by weight water/methyl ester C8-C10 in the range of 0.4-1.5;
   separating aqueous and organic phase through a second Vapor/Liquid/Liquid separator (S2);
   c) using the organic phase of b) as charge for a third hydrolysis step, in a consecutive hydrolyzing reactor (R3), adding a quantity of water to the sample to keep the ratio by weight water/methyl ester C8-C10 in the range of 0.4-1.5;
   separating aqueous and organic phase through a third Vapor/Liquid/liquid separator (S3).

6. The autocatalytic process for producing fatty acids from fatty acids methyl esters with an overall conversion higher than 90% according to claim 5 wherein the ratio by weight water/methyl ester in each of the three hydrolysis steps is equal to 0.9.

7. The autocatalytic process for producing fatty acids from fatty acids methyl esters with an overall conversion higher than 90% according to claim 5 wherein the step c) is repeated "n" times.

8. The autocatalytic process for producing fatty acids from fatty acids methyl esters with an overall conversion higher than 90% according to claim 5, further comprising carrying out a distillation of the organic phases containing C8-C10 fatty acids out coming from a last separator.

9. The autocatalytic process according to claim 1 where hydrolysis reaction temperatures have been selected in the range 130-300° C.

10. The autocatalytic process according to claim 1 where temperatures of phases after the separation reaction have been selected in the range 50-150° C.

11. The autocatalytic process according to claim 1 where hydrolysis reaction pressures have been selected in the range 10-100 Bar.g.

12. The autocatalytic process according to claim 1 where distillation pressures of produced fatty acids have been selected in the range 0-2000 mBar.a.

13. The autocatalytic process according to claim 1, wherein a light cut obtained by distillation, being a mixture of not reacted C8-10 methyl-esters, is recycled to the reaction steps.

14. The autocatalytic process according to claim 1, wherein an achieved purity of C8-10 Fatty acids is higher than 99% w/w.

15. An apparatus as defined for the process according to claim 1 for producing fatty acids from fatty acids methyl esters with an overall conversion higher than 90%, the apparatus comprising a plurality of hydrolysis reactors in series to carry out the hydrolysis of fatty acids methyl esters auto catalytically, in purely thermal conditions, wherein each hydrolysis reactor is immediately followed by Liquid vapor separators in order to separate, after each hydrolysis reaction step, aqueous phase, that is discharged, and organic phase, that is fed as reactant in the subsequent hydrolysis reactor, to increase the amount of fatty acids in the solution.

16. The apparatus for producing fatty acids from fatty acids methyl esters with an overall conversion higher than 90% according to claim 15, further comprising a distillation column to carry out a liquid/liquid separation of organic phase coming out from the a last separator.

17. The apparatus for producing fatty acids from fatty acids methyl esters according to claim 16 wherein the distillation column is under vacuum at a total pressure in the range 0-0.5 bar.

18. The apparatus for producing fatty acids from fatty acids methyl esters according to claim 16 wherein the distillation column is under vacuum at a total pressure of 0.02 bar.

19. The apparatus of claim 15, wherein the hydrolysis reaction units are integrated with at least a methanol rectification column to produce pure methanol and recover the excess of water to be recirculated back to the reaction units.

20. The apparatus of claim 15 comprising means to select a hydrolysis reaction temperature and a separation temperature.

21. The apparatus of claim 15 wherein the hydrolysis reactor is a sealed high pressure stainless steel reactor.

22. The autocatalytic process according to claim 9, wherein a hydrolysis reaction temperatures are in a range of 150-250° C.

23. The autocatalytic process according to claim 10, wherein a temperatures of phases after the separation reaction are in a range of 80-110° C.

24. The autocatalytic process according to claim 11, wherein a hydrolysis reaction pressures are in a range of 40-60 Bar.g.

25. The autocatalytic process according to claim 12, wherein a distillation pressures of produced fatty acids are in a range of 50-400 mBar.a.

26. The autocatalytic process according to claim 14, wherein an achieved purity of C8-10 Fatty acids is higher than 99.5% w/w.

* * * * *